US010067124B2

(12) United States Patent
Yoshimura et al.

(10) Patent No.: US 10,067,124 B2
(45) Date of Patent: Sep. 4, 2018

(54) IMMUNOASSAY METHOD FOR PRO-GASTRIN-RELEASING PEPTIDE

(71) Applicants: Abbott Laboratories, Abbott Park, IL (US); Abbott Japan Co. Ltd., Tokyo (JP)

(72) Inventors: Toru Yoshimura, Chiba (JP); Kenju Fujita, Chiba (JP); Barry L. Dowell, Mundelein, IL (US)

(73) Assignees: Abbott Laboratories, Abbott Park, IL (US); Abbott Japan Co. Ltd., Tokyo (JP)

(*) Notice: Subject to any disclaimer, the term of this patent is extended or adjusted under 35 U.S.C. 154(b) by 0 days.

(21) Appl. No.: 15/283,828

(22) Filed: Oct. 3, 2016

(65) Prior Publication Data

US 2017/0089889 A1    Mar. 30, 2017

Related U.S. Application Data

(63) Continuation of application No. 14/295,116, filed on Jun. 3, 2014, now Pat. No. 9,459,248, which is a (Continued)

(30) Foreign Application Priority Data

Dec. 11, 2006  (JP) ................. 2006-333072

(51) Int. Cl.
*G01N 33/86*   (2006.01)
*G01N 33/53*   (2006.01)
*G01N 33/574*  (2006.01)

(52) U.S. Cl.
CPC ... *G01N 33/5306* (2013.01); *G01N 33/57423* (2013.01); *G01N 33/86* (2013.01); *G01N 2333/5758* (2013.01)

(58) Field of Classification Search
CPC ......... G01N 33/5306; G01N 33/57423; G01N 33/86; G01N 2333/5758
See application file for complete search history.

(56) References Cited

U.S. PATENT DOCUMENTS 5,256,540 A * 10/1993 Lennon ............ C01N 33/57423
                                                      435/7.23
5,770,385 A *  6/1998 Yamaguchi ...... C07K 14/57572
                                                        435/325

(Continued)

FOREIGN PATENT DOCUMENTS

JP    2003-270238    *  3/2003   ............. G01N 33/48
JP    2003-270238        9/2003

(Continued)

OTHER PUBLICATIONS

Boyanton, B.L. et al., "Stability studies of twenty-four analytes in human plasma and serum," Clin. Chem. (2002) 48:2242-2247.

(Continued)

*Primary Examiner* — Gailene Gabel
(74) *Attorney, Agent, or Firm* — Melissa E. Kolom; Casimir Jones, S.C.

(57) ABSTRACT

To provide a more convenient and more accurate method of assaying ProGRP by improving the stability of ProGRP which is known to be unstable in a biological sample.
By using a blood sample in a condition in which a blood coagulation factor is not activated is used as a sample, the degradation of ProGRP is suppressed, whereby it is possible to store a sample for a long period of time and to improve the accuracy of an assay.

2 Claims, 10 Drawing Sheets

Related U.S. Application Data continuation of application No. 12/518,610, filed as application No. PCT/JP2007/073854 on Dec. 11, 2007.

(56) References Cited

U.S. PATENT DOCUMENTS

| | | | |
|---|---|---|---|
| 7,927,814 B2 | 4/2011 | Aoyagi | |
| 2008/0160545 A1* | 7/2008 | McKeegan | G01N 33/574 435/7.23 |

FOREIGN PATENT DOCUMENTS

| | | |
|---|---|---|
| WO | 2006/117994 | 11/2006 |
| WO | 2008/029965 | 3/2008 |
| WO | 2008/072621 | 6/2008 |

OTHER PUBLICATIONS

Evans, M.J. et al., "Effect of anticoagulants and storage temperatures on stability of plasma and serum hormones," Clin. Biochem. (2001) 34:107-112.

Aoyagi, K. et al., "Enzyme immunoassay of immunoreactive progastrin-releasing peptide (31-98) as tumor marker for small-cell lung carcinoma: development and evaluation," (1995) 537-543.

Holst, J.J. et al., "Elevated plasma concentrations of C-flanking gastrin-releasing peptide in small-cell lung cancer," J. Clin. Oncology (1989) 7(12):1831-1838.

Drivsholm, L., "Gastrin-releasing peptide (GRP) and pro-gastrin-releasing peptide (Pro-GRP) measured in the plasma of 169 patients with small cell lung cancer (SCLC)," Lung Cancer (1991) 7(1):54.

Yoshimura, T. et al., "Stability of pro-gastrin-releasing peptide in serum versus plasma," Tumor Biology (2008) 29 (4):224-230.

Yoshimura, T. et al., "Initial performance characteristics of a prototype ARCHITECH (R) ProGRP assay," Tumor Biology (2006) 27(Supp2), 34th Meeting of the International Society for Oncodevelopmental Biology and Medicine, Pasadena, CA Sep. 16-20, 2006.

Yoshimura, T. et al., "Stability of pro-gastrin releasing peptide in serum and plasma," Tumor Biol. (2007) 109.

European Patent Office Action for Application No. 07850416.4 dated Jun. 2, 2010 (8 pages).

European Patent Office Action for Application No. 07850416.4 dated Mar. 14, 2011 (4 pages).

International Preliminary Report on Patentability for Application No. PCT/JP2007/073854 dated Aug. 28, 2009 (English translation version).

International Search Report for Application No. PCT/JP2007/073854 dated Jan. 22, 2008 ( English translation).

European Patent Office Action for Application No. 07850416.4 dated Oct. 22, 2014 (5 pages).

* cited by examiner

IMMUNOASSAY METHOD FOR PRO-GASTRIN-RELEASING PEPTIDE

CROSS-REFERENCE TO RELATED APPLICATION(S)

This application is a continuation of U.S. patent application Ser. No. 14/295,116, filed on Jun. 3, 2014, which issued as U.S. Pat. No. 9,459,248 on Oct. 4, 2016, which is a continuation of U.S. patent application Ser. No. 12/518,610, filed on Jan. 14, 2010, now abandoned, which is a U.S. national stage entry of International Patent Application No. PCT/JP2007/073854, filed on Dec. 11, 2007, which claims priority to Japanese Patent Application No. 2006-333072, filed on Dec. 11, 2006, the entire contents of all of which are fully incorporated herein by reference.

TECHNICAL FIELD

The present invention relates to an assay method in which plasma is used as a sample and the sample stability is remarkably improved in a system for detecting ProGRP (pro-gastrin-releasing peptide) by an immunoassay.

BACKGROUND ART

The usefulness of the relationship between lung cancer and the concentration of blood gastrin-releasing peptide (GRP) has been known as reported by also Yamaguchi et al. (see Patent document 1). However, GRP is a physiologically active substance and loses its activity in an extremely short period of time in serum or plasma. Therefore, it was difficult to practically use it as an immunoassay. Yamaguchi et al. found that the antigen stability sufficient to withstand the practical use as an immunoassay can be achieved by specifically assaying, among three types of pro-gastrin-releasing peptides (ProGRPs) which are precursors of GRP, an amino acid sequence of residues 31-98 (ProGRP 31-98) which does not contain a physiologically active region (an amino acid sequence of residues 1-27) and is a region common to the three types, and found that it is useful for diagnosis of lung cancer (see Patent document 1). According to this method, ProGRP can stably exist in serum or plasma equally up to 6 hours, therefore, it became possible to put it to practical use as an immunoassay method. Further, because an advantage of the use of plasma is not particularly obtained, serum which is generally used for assaying a cancer marker has come to be used as a sample.

PATENT DOCUMENT 1

JP-A-6-98794

DISCLOSURE OF THE INVENTION

Problems that the Invention is to Solve

However, the stability of ProGRP 31-98 is still inferior to a general antigen to be used in an immunoassay. An acceptable degree of decrease in the activity of ProGRP 31-98 in a sample seems to vary depending on the manufacturer thereof. However, in the case of Immucheck F-ProGRP available from Sysmex Corporation, a sample is allowed to be stored under refrigeration for at most 3 hours, in the case of a Serumlabo (registered trademark) ProGRP assay kit available from Fujirebio Inc., a sample is allowed to be stored under refrigeration for at most about 24 hours (either of them is a diagnostic agent which has been already approved by the Ministry of Health, Labour and Welfare), and both products do not allow the storage at room temperature. Further, it is construed that the stabilities thereof in plasma and serum are equal, therefore, only an assay using serum has been put in practical use. In the case where a serum sample is stored for 3 hours to more than 24 hours, it is necessary to freeze the sample. Therefore, labors of thawing the sample before use, removing a deposited matter generated by freezing and thawing by centrifugation before the assay are required, and so on, such insufficient sample stability significantly lowered the working efficiency. Further, many of the antigens including typical cancer markers such as CEA, AFP and CA 19-9, which are immunologically assayed, can stably exist up to 7 days in refrigeration storage. Therefore, only in the case where this assay is carried out, special operation and storage place are required, and so on, it has also become a cause that lowers the efficiency of the test as a whole.

It has been construed that the reason why the sample stability of ProGRP 31-98 is low is because the molecular weight thereof is low. Further, because a significant difference was not observed between the assay values of ProGRP 31-98 in serum and plasma in the range up to 6 hours, in which only a slight decrease in the activity thereof was observed even in serum, it was not considered that there was a difference in stabilities between serum and plasma.

Means for Solving the Problems

ProGRP is a protein having a molecular weight of 8000 to 10000, and a domain of an amino acid sequence of residues 31-98 with which an assay is carried out in an immunoassay of ProGRP 31-98 has a molecular weight of about 7800. It is known that the sample stability of a peptide molecule having a low molecular weight is low as a general fact, and it can be understood that a study of examining the cause of the low sample stability of ProGRP has not been reported. However, even in the case where a molecular weight is low like insulin (molecular weight: 5800) or the like to be used as an immunodiagnostic agent, a peptide molecule that can stably exist in serum or plasma for more than 5 days in refrigeration storage exists, therefore, the inventor thought that there must be some kind of mechanism of sample instability, which is unique to ProGRP, in addition to its low molecular weight.

The inventors thought that because the ProGRP molecule per se can stably exist in refrigeration storage for more than about 1 week, it is not only attributable to ProGRP per se that makes it unstable in a sample, and there may be a substance which is present in blood and makes it unstable. Further, the inventor thought that because a GRP portion which is a physiologically active region (an amino acid sequence of residues 1 to 27) is not already contained in ProGRP 31-98, there may be a possibility that some kind of reaction other than a reaction occurring in vivo causes the sample instability unique to ProGRP.

As described in a standard book, when blood comes out of the body, more than 10 substances called blood coagulation factors and fibrinolytic factors are activated, and these respective substances induce degradation or activation of precursor molecules of blood coagulation factors, and in the end, induce activation of thrombin generated by the degradation of prothrombin and formation of fibrin generated by the degradation reaction of fibrinogen by thrombin thereby to coagulate blood, which is a well-known fact. A liquid component obtained by removing a portion coagulated at this time results in serum. Most of the activators of such blood coagulation factors are proteases including thrombin and exist in serum. In plasma, the activation of thrombin is not caused, and further, the activation of several blood coagulation factors is not caused, although it depends on the anticoagulant. That is, in serum, activators and degraders of blood coagulation factors and fibrinolytic factors exist at a higher level in serum than in vivo or in plasma. Thus, the inventors presumed that there may be a relationship between such a substance that exists in serum and does not exist or exists only at a low level in vivo and the instability of ProGRP 31-98.

In accordance with this presumption, the inventor examined a decrease in the activity of thrombin, which is an activator of a blood coagulation factor, by adding it to a ProGRP solution, and observed a significant decrease in the activity of ProGRP in the solution with the addition of thrombin. Accordingly, it was found that thrombin, which is an activator of a blood coagulation factor, is one of the causes of the decrease in the activity of ProGRP.

The inventor examined the stability of ProGRP by using plasma as a sample with the use of a property that activators of blood coagulation factors exist at a high level in serum and do not exist or exist only at a low level in vivo or in plasma, and succeeded in remarkably improving the sample stability of ProGRP, thus the present invention has been completed. It is possible to collect plasma from blood in a similar manner to serum, and plasma can be collected from blood in a substantially similar manner to serum, and can be used in an immunoassay without any problems. Further, by adding an inhibitor or an inactivator of such an activator of a blood coagulation factor or a fibrinolytic factor to a serum sample, a similar effect can be obtained.

Constitution of the Invention

The present invention provides, based on the above-mentioned findings, a method of assaying ProGRP with which a more convenient and more accurate assay than a conventional method can be achieved by using a blood sample in a condition in which a blood coagulation factor is not activated, whereby fibrin formation is not caused and blood coagulation does not occur.

The phrase, "a blood sample in a condition in which one or more blood coagulation factors are not activated" means a blood sample in a condition in which an agent that suppresses or lowers the activation of any blood coagulation factor is added or a blood coagulation factor is removed. As the agent that suppresses or lowers the activation of a blood coagulation factor, an agent such as EDTA, heparin, or citric acid can be used, however, it is not limited to these.

Accordingly, as the blood sample in a condition in which blood coagulation does not occur, it is typical to use plasma. As the plasma described here, any plasma sample to be used in a test can be used. That is, typical examples thereof include EDTA plasma, heparin plasma and citric acid plasma, and also include other plasmas. Further, as for a salt to be used for each substance, an arbitrary salt can be selected. As for EDTA, typical examples thereof include 2K, 3K and the like. As for heparin, typical examples thereof include a sodium salt, a lithium salt and the like. However, other salts can also be selected.

Further, it is also possible to obtain an effect by adding a substance that inactivates a blood coagulation factor to serum after collecting the serum, removing a blood coagulation factor, or lowering the activity thereof It is proper to employ the present invention in an immunoassay method, however, the present invention can also be employed in any assay system for performing a ProGRP assay.

Advantage of the Invention

According to the present invention, a sample can be stably stored for a long period of time. The storage period thereof in refrigeration storage can be prolonged from 3 to 24 hours in a conventional method to about 1 week. Further, it is also possible to store a sample at room temperature.

According to the present invention, it is not necessary to cryopreserve a sample even in the case where the storage time of the sample exceeds 3 to 24 hours. Therefore, labors of thawing the sample before use when the sample is frozen, removing a deposited matter generated by freezing and thawing by centrifugation are not required, and so on, the working efficiency can be significantly improved. Further, it becomes possible to store a sample for 1 week for which many of the other antigens to be immunologically assayed can be stably stored in refrigeration storage, therefore, a special storage operation and storage place for a sample for assaying ProGRP are not required.

Further, the present invention improves the long-term stability of a sample in cryopreservation, and moreover, it improves the stability thereof at room temperature, therefore, labors of performing serum separation or storage in refrigeration conditions can be omitted. Further, in the present invention, a decrease in the activity during the operation at room temperature which cannot be avoided during the process of operation from blood collection to completion of assaying can be suppressed. Therefore, it becomes possible to assay ProGRP values more accurately.

It is considered that an instability degree of ProGRP in serum varies among patients as a matter of course. Accordingly, it is conceivable that in the case of a conventional method using serum as a sample, by the decrease in the activity of ProGRP antigen during the process of serum separation or storage, the serum exhibits a negative value upon assaying although it essentially has ProGRP corresponding to a positive value. It is considered that such occurrence of false negative test results for the antigen activity can be prevented by employing the present invention, and thereby the detection sensitivity of small cell lung cancer can be improved.

Incidentally, as the method of assaying ProGRP, there are a number of documents, however, as an example in which plasma is used as a sample, there is only one report by Yamaguchi et al. However, this report only leads to the conclusion that serum and plasma are equal in terms of the sample stability, and it does not at all suggest the superior usefulness of plasma in the present invention. Further, documents that describe stability studies involved in other substances between serum and plasma are shown below, however, it is obvious that they do not at all suggest the assay method of the present invention.

Yamaguchi et al. (Japanese Patent No. 3210994) found a relationship between ProGRP 31-98 and diagnosis of lung cancer and shows that a plasma sample can be used in the same manner as a serum sample up to a storage time of 6 hours. However, there is no description of the superiority of a plasma sample in terms of the storage stability. It is a work commonly performed in an immunoassay that the equivalence between plasma and serum as a sample subjected to an immunoassay is shown by using both plasma and serum, and the constitution of the invention of this application that plasma has a superior usefulness is not inferable easily from this document even by those skilled in the art.

Evans et al. (Clinical Biochemistry Vol. 34, pp. 107-112, 2001) examined the stability of a hormone having a physiological activity in serum and plasma and has reported that which of serum and plasma is better in terms of the stability of the hormone varies depending on the type of the hormone. This shows that from the viewpoint of the stability of a test substance, a serum sample can be rather better than a plasma sample, which prevents those skilled in the art from arriving at the present invention of this application instead.

Boyanton et al. (Clinical Chemistry Vol. 48, pp. 2242-2247, 2002) studied the stabilities of 24 types of substances in serum and plasma. They showed that in either of the cases of scrum and plasma, when serum separation or plasma separation from blood cells was carried out immediately after blood collection, the substances could be stably exist for 58 hours or more in either of serum and plasma. In addition, it concluded that when separation was not carried out, the stability of the substances was better in serum. In this document, there is no description related to ProGRP and also it concluded that the stability is better in serum, therefore, we have no doubt that our invention has novelty.

Further, at present, three types of ProGRP diagnostic agents have been approved by the Ministry of Health, Labour and Welfare and are available on the market and used in the clinical fields (medical coverage started in 1996). However, there is no report that the stability of ProGRP 31-98 in plasma is better than in serum. Therefore, it can be said that this is clear evidence showing that the present invention has novelty.

The invention of this application that the stability of a sample is improved by using a sample in a condition in which blood coagulation does not occur is a novel invention based on a mechanism which is totally different from any prior art, and exhibits an effect which could not be expected in the prior art.

EXAMPLES

Example 1

Relationship Between Instability of ProGRP Antigen and Thrombin

ProGRP 31-98 antigen (obtained from Abbott Laboratories in the U.S.A.) amino acid synthesized by the Fmoc method was added to a phosphate buffer solution containing 1% bovine serum albumin and 2 mM calcium chloride. Thrombin (manufactured by Sigma-Aldrich Co.) was further added thereto and after the mixture was stored at room temperature, the concentration of ProGRP was assayed using an Architect ProGRP. The assay results are shown in FIG. 1. From FIG. 1, because the degradation of ProGRP is observed in the presence of thrombin, it is suggested that thrombin be related as a major cause of the degradation of ProGRP in serum. Thrombin is the activator of blood coagulation factor II and is a substance which exists in serum at a high level. The details of the Architect assay method are described in Example 3.

Example 2

Stabilization of ProGRP by Addition of PMSF (Phenylmethanesulfonyl Fluoride)

After PMSF (manufactured by Sigma-Aldrich Co.) was added to serum, ProGRP 31-98 antigen amino no acid synthesized by the Fmoc method was added thereto. After the mixture was stored at room temperature, the concentration of ProGRP was assayed using the Architect ProGRP. The assay results are shown in FIG. 2. From FIG. 2, it is found that a decrease in the activity of ProGRP is significantly suppressed in the presence of PMSF. PMSF is a substance that is used to inactivate the activity of an enzyme of a serine protease such as thrombin and the presence of a protease such as thrombin can be considered to be the cause of ProGRP inactivation.

Example 3

Stabilization of ProGRP Antigen Using Plasma

ProGRP 31-98 antigen (obtained from Abbott Laboratories in the U.S.A.) synthesized by the Fmoc method was added to each of the serum and EDTA plasma obtained from the same blood donor and the mixtures were used as assay samples. After the assay samples were stored under refrigeration for 1 day, 3 days or 7 days, or stored for 1 day at room temperature, the concentration of ProGRP was assayed. For the assay of the concentration of ProGRP, a Serumlabo (registered trademark) ProGRP assay kit (Fujirebio Inc.) and the Architect ProGRP described below were used. The assay results are shown in FIG. 3 to FIG. 7.

Both the Serumlabo ProGRP and the Architect ProGRP are a method of assaying the concentration of ProGRP 31-98 utilizing an immunoassay and the assay results of both were equivalent. In both cases, when ProGRP antigen was allowed to exist in plasma, a significant improvement of sample stability was observed compared with the case of serum. This significant improvement of stability could be observed not only in refrigeration storage but also in room temperature storage.

Although ProGRP can be stably stored for 1 day (until the following day) under the refrigeration storage condition in the method using serum, it can be stably stored for 1 week or more in the case where plasma is used. The time required for a residual ratio to show 90% when a ProGRP residual ratio is approximated as ProGRP residual ratio=$e^{kt}$ (e: natural log, k: numerical constant, t: time) in accordance with an approximation formula for an inactivation ratio of a general substance shown by Evans et al. (Clinical Biochemistry, vol. 34, pp. 107-112, 2001) is calculated to be 10.25 days under refrigeration when the assay value of a sample stored under refrigeration for 7 days using a Serumlabo (registered trademark) ProGRP assay kit is used. In a similar manner, the time is calculated to be 1.26 days in the case of serum (the assay value of a serum sample stored under refrigeration for 1 day using a Serumlabo (registered trademark) ProGRP assay kit is used for the calculation). Thus, it is found that in the case where plasma is used, the stability thereof about 8 times as high as that of serum can be obtained.

In the currently available methods using serum, a ProGRP sample cannot be stably stored at room temperature. In the case where plasma is used, it can be stably stored for 24 hours or more. The time required for a residual ratio to show 90% when a ProGRP residual ratio is approximated as ProGRP residual ratio=$e^{kt}$ (e: natural log, k: numerical constant, t: time) is calculated to be 58 hours when the assay value of a sample stored at room temperature for 24 hours using Serumlabo is used, and it is possible to stably store a sample up to about 2 days even in room temperature storage.

Architect ProGRP Assay Method

An anti-ProGRP 31-98 antibody (an antibody obtained in accordance with the method described in Japanese Patent No. 3210994) was bound to a carboxyl group-modified magnetic microparticle (obtained from Abbott Laboratories in the U.S.A.) by a method using EDC (N-ethyl-N'-(3-dimethylarninopropyl)carbodiimide hydrochloride (manufactured by Sigma-Aldrich Co.) and an antibody solid-phased microparticle was prepared. Then, by adding the antibody solid-phased microparticle to a Tris-HCl buffer solution containing Tween 20 (manufactured by Kanto Chemical Co., Inc.), EDTA (ethylenediamine tetraacetic acid sodium salt) and sodium chloride, an antibody solid-phased microparticle solution was prepared.

The anti-ProGRP 31-98 antibody (an antibody obtained in accordance with the method described in Japanese Patent No. 3210994) was labeled with an acridinium derivative (obtained from Abbott Laboratories in the U.S.A.), and then by adding it to an MES buffer solution containing a surfactant and bovine serum albumin (Sigma-Aldrich Co.), a labeling solution was prepared.

For an assay for the concentration of ProGRP, an Architect full automatic immunoassay analyzer (manufactured by Abbott Japan Co., Ltd.) was used. 50 µl of the antibody solid-phased microparticle solution was mixed with 50 µl of a sample and a first reaction was started. During the first reaction, ProGRP antigen binds to the antibody solid-phased magnetic particle and the amount bound corresponds to the concentration of ProGRP in the sample. After 18 minutes, while being held by a magnet, the antibody solid-phased magnetic particle was washed with a phosphate buffer solution dedicated to this device and 50 µl of the labeling solution was further added thereto and the reaction was continued for an additional 4 minutes. By this reaction, the labeled antibody binds to the ProGRP on the magnetic particle. Because the amount of labeled antibody bound corresponds to the amount of ProGRP on the magnetic particle, if the concentration of ProGRP in the sample is low, a small amount of labeled antibody results in binding to the magnetic particle and if the concentration of ProGRP in the sample is high, a large amount of labeled antibody results in binding to the magnetic particle.

Then, after washing is carried out with the phosphate buffer solution dedicated to this device, a luminescence signal was observed using a luminescence pretrigger reagent and a trigger reagent dedicated to this device. By using a solution with a known concentration prepared separately as a standard solution, a standard curve was prepared by the four parameter logistic method, and by calculating a signal obtained from the sample into the concentration of ProGRP, the concentration of ProGRP in the sample was determined.

Example 4

Comparison of a Variety Types of Plasmas

Recombinant ProGRP 31-98 obtained in accordance with the method described in Japanese Patent No. 3210994 was added to each of matched samples of EDTA plasma, lithium heparin plasma, citric acid plasma, sodium heparin plasma and serum obtained from the same blood donor and the mixtures were stored at room temperature for 24 hours or stored under refrigeration for 7 days and the concentration of ProGRP was assayed in the same manner as described in Example 3. From the assay value of the sample left at room temperature for 24 hours, the assay value of 0 hour was subtracted, and the resulting value was taken as a ProGRP residual ratio after 24-hour room temperature storage. From the assay value of the sample stored under refrigeration for 7 days, the assay value of 0 hour was subtracted, and the resulting value was taken as a ProGRP residual ratio after 7-day refrigeration storage.

In FIG. 7, the ProGRP residual ratio in each plasma after 7-day refrigeration storage is shown. In FIG. 8, the ProGRP residual ratio in each plasma after 24-hour room temperature storage. From FIGS. 7 and 8, the ProGRP residual ratios are significantly higher in any of the plasmas compared with in serum and, in other words, it is obvious that the sample stability is significantly improved in any of the plasmas. In addition, because the residual ratios are almost 100% in 7-day refrigeration storage in plasma, it is obvious that almost total amount of ProGRP is stably stored in plasma up to 7 days under refrigeration.

Example 5

Time Course

ProGRP 31-98 antigen amino acid synthesized by the Fmoc method was added to each of matched samples of EDTA plasma and serum obtained from the same blood donor and the mixtures were stored at room temperature or under refrigeration and the concentration of ProGRP was assayed by the method described in Example 3. The values up to 24 hours are shown by the average of 3 donors and the values up to 72 hours are shown by the average of 2 donors. The ProGRP residual ratios in refrigeration storage and the ProGRP residual ratios in room temperature storage are shown in FIG. 9 and FIG. 10, respectively. The storage times shown in the drawings are 0, 1, 3, 6, 7, 9 and 24 hours (both refrigeration storage and room temperature storage until this time) and 72 hours (only refrigeration storage).

From FIG. 9, as Yamaguchi et al. shows, in refrigeration storage, serum and plasma have an equivalent ProGRP stability in storage up to 6 hours. However, the difference gradually becomes significant after 6 hours, and when a ProGRP sample is stored for 24 hours or more, plasma apparently can show better stability than serum.

From FIG. 10, in room temperature storage, a significant difference in the stability of ProGRP between serum and plasma has already occurred at the time that exceeds 3 hours. In addition, when a sample is stored for 6 hours or more, it is obvious that plasma can show apparently better storage stability than serum. In the case where ProGRP is stored in serum, the activity of ProGRP decreases to about 80% at the time of 6-hour storage. When a sample is stored for the purpose of a diagnostic agent, generally a residual activity up to 90% (a decrease in the activity by 10%) is the acceptable limit. Because in the case where a sample is stored at room temperature in serum, the activity of ProGRP decreases to about 80% at the time of 6-hour storage, it can be said that the result shown in FIG. 10 is consistent with the description matter in the Seruinlabo (registered trademark) ProGRP assay kit and the Immucheck F-ProGRP kit of the approved products which do not allow room temperature storage. On the other hand, in the case where ProGRP is stored in plasma, the residual ratio of activity is about 90% even in the case where it is stored for 24 hours even in room temperature storage, therefore, it is considered that stable storage up to about 24 hours can be achieved. Yamaguchi et al. shows that plasma can be used within the range that allows ProGRP to exist stably in serum, however the present invention is different from the invention of Yamaguchi et al. in the point that the storage stability of ProGRP in a blood sample that is sufficient to he used for the purpose of a diagnostic agent can be secured even in a storage condition or storage time in which ProGRP cannot stably exist in serum and it is considered that the usefulness of the present invention can be shown.

Figure 1:
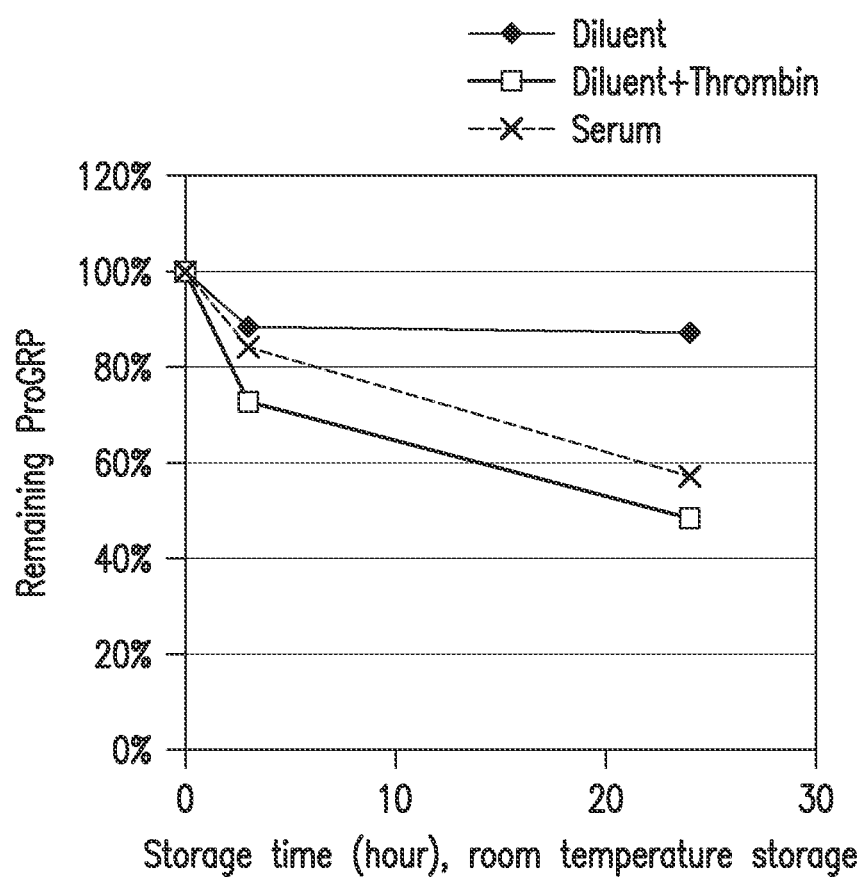
FIG. 1 depicts a plot of the remaining ProGRP (expressed as %) as a function of storage time (expressed in hours) at room temperature for ProGRP antigen incubated in samples containing diluent (♦), diluent including Thrombin (□), or serum (x).
Figure 2:
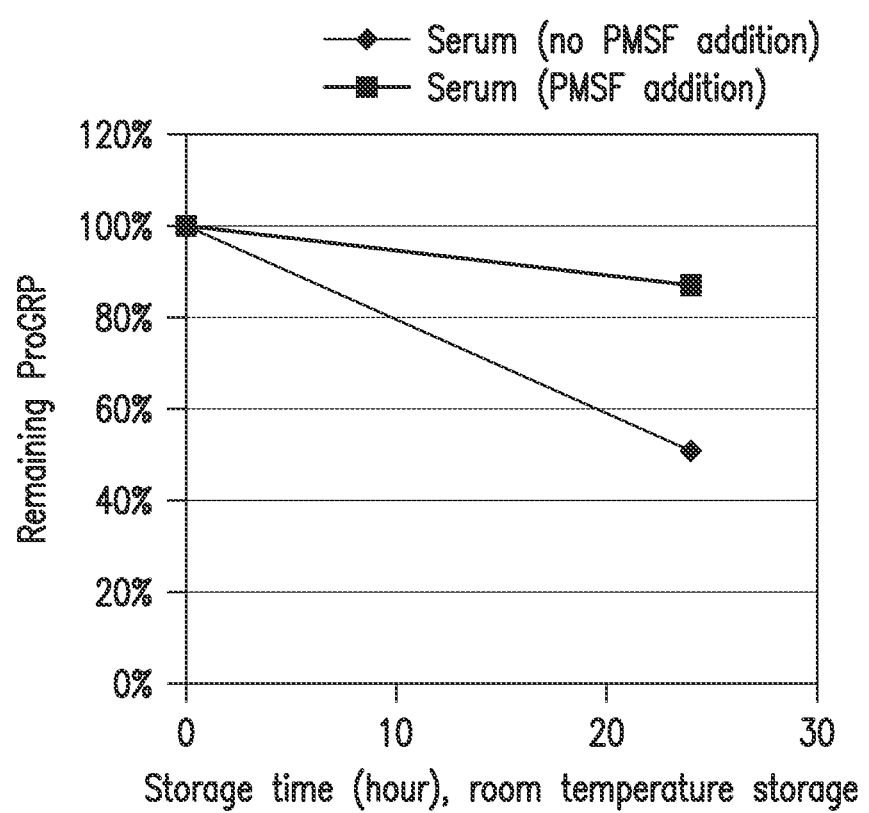
FIG. 2 depicts a plot of the remaining ProGRP (expressed as %) as a function of storage time (expressed in hours) at room temperature for ProGRP antigen incubated in samples containing serum lacking PMSF (♦) or serum including PMSF (■).
Figure 3:
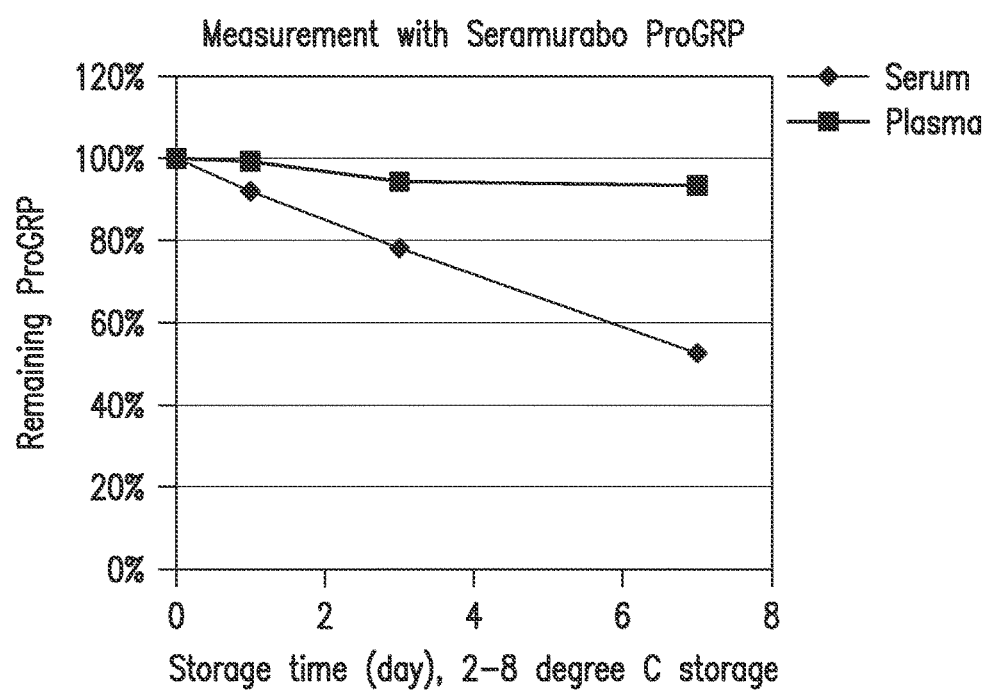
FIG. 3 depicts a plot of the remaining ProGRP (expressed as %) as a function of storage time (expressed in days) at refrigeration temperature (2 °C.-8 °C.) for ProGRP antigen incubated in samples containing serum (♦) or plasma (■), as measured using the Serum-Labo ProGRP assay kit.
Figure 4:
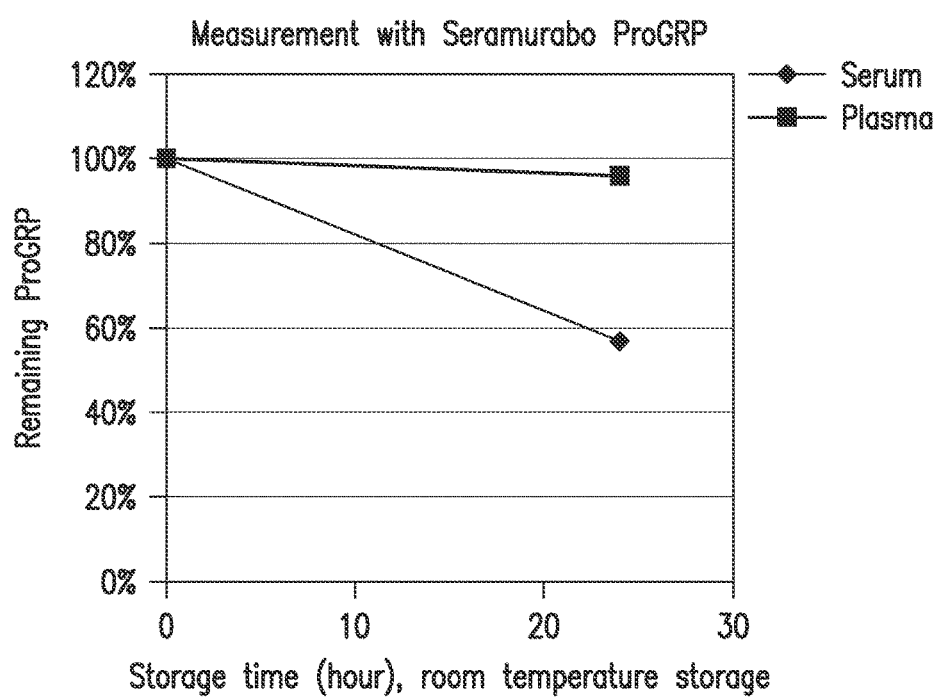
FIG. 4 depicts a plot of the remaining ProGRP (expressed as %) as a function of storage time (expressed in hours) at room temperature for ProGRP antigen incubated in samples containing serum (♦) or plasma (■), as measured using the Serum-Labo ProGRP assay kit.
Figure 5:
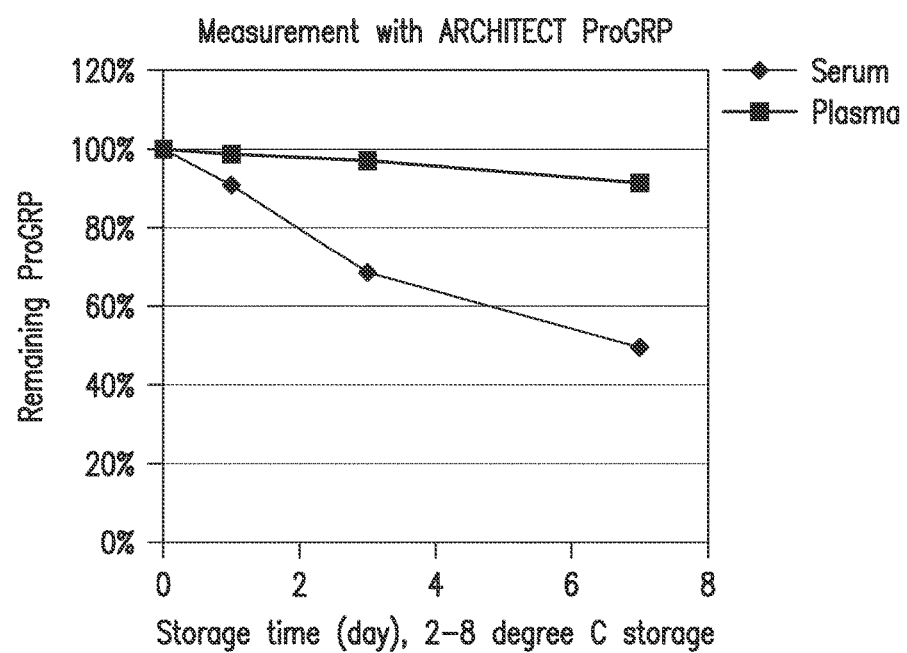
FIG. 5 depicts a plot of the remaining ProGRP (expressed as %) as a function of storage time (expressed in days) at refrigeration temperature (2 °C.-8 °C.) for ProGRP antigen incubated in samples containing serum (♦) or plasma (■), as measured using the ARCHITECT® ProGRP assay kit.
Figure 6:
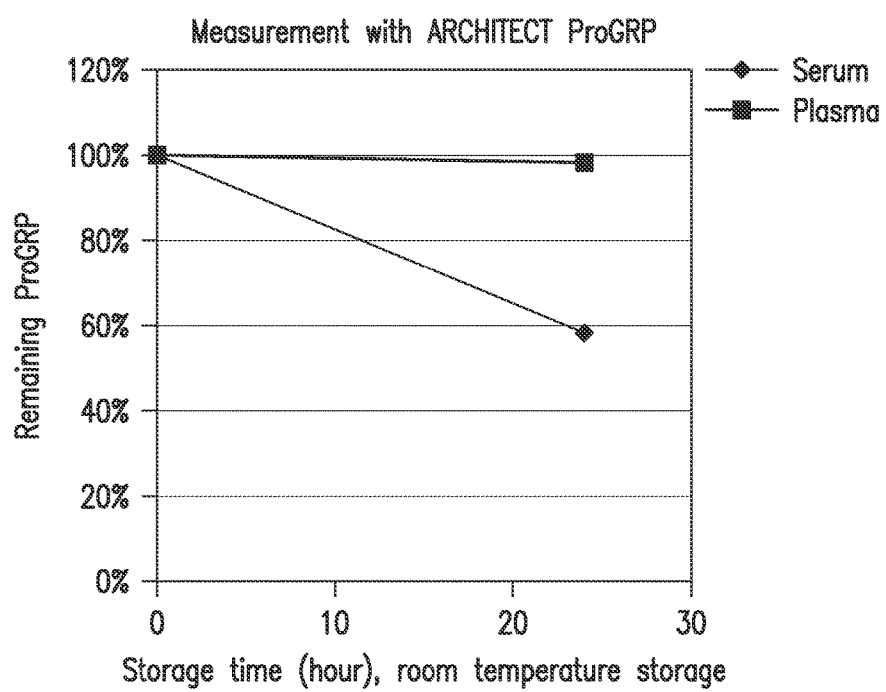
FIG. 6 depicts a plot of the remaining ProGRP (expressed as %) as a function of storage time (expressed in hours) at room temperature for ProGRP antigen incubated in samples containing serum (♦) or plasma (■), as measured using the ARCHITECT® ProGRP assay kit.
Figure 7:
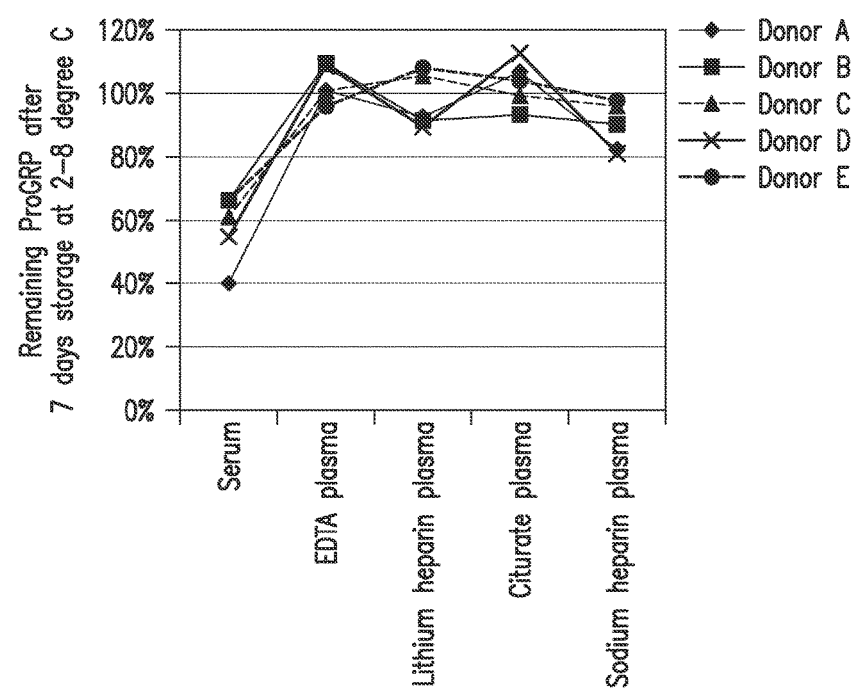
FIG. 7 depicts a graph of the remaining ProGRP after 7 days of storage at refrigeration temperature (2 °C.-8 °C.) for different donor samples [A(♦), B (■), C (▲), D (x) and E (●)], wherein the donor samples are incubated in the presence of serum, or plasma including either EDTA ("EDTA plasma"), lithium heparin ("lithium heparin plasma"), citric acid ("citric acid plasma"), or sodium heparin ("sodium heparin plasma").
Figure 8:
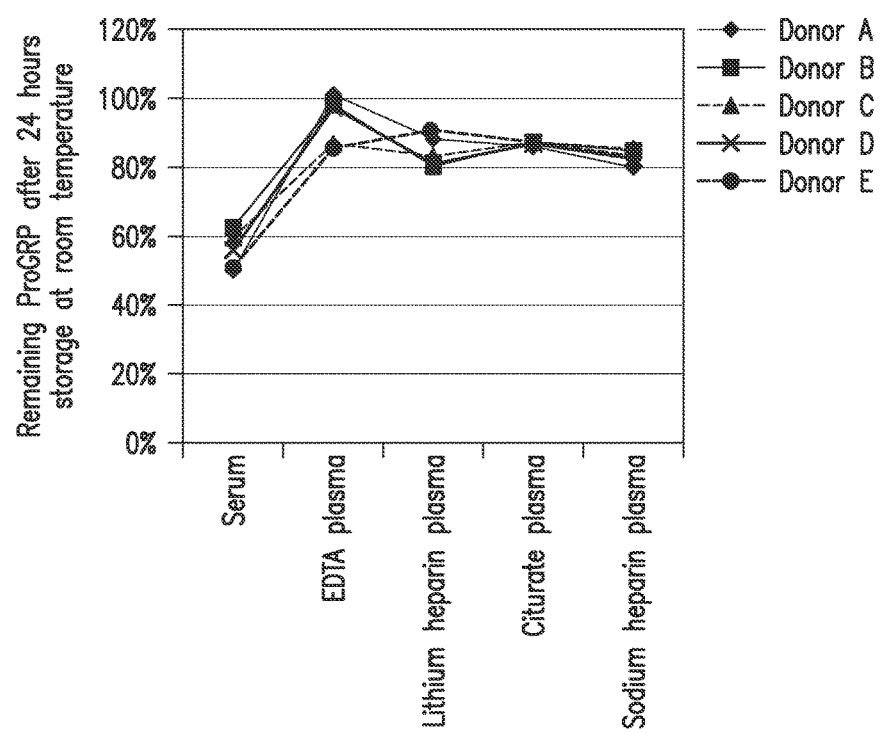
FIG. 8 depicts a graph of the remaining ProGRP after 24 hours of storage at room temperature for different donor samples [A (♦), B (■), C (▲), D (x) and E (●)], wherein the donor samples are incubated in the presence of serum, or plasma including either EDTA ("EDTA plasma"), lithium heparin ("lithium heparin plasma"), citric acid ("citric acid plasma"), or sodium heparin ("sodium heparin plasma").
Figure 9:
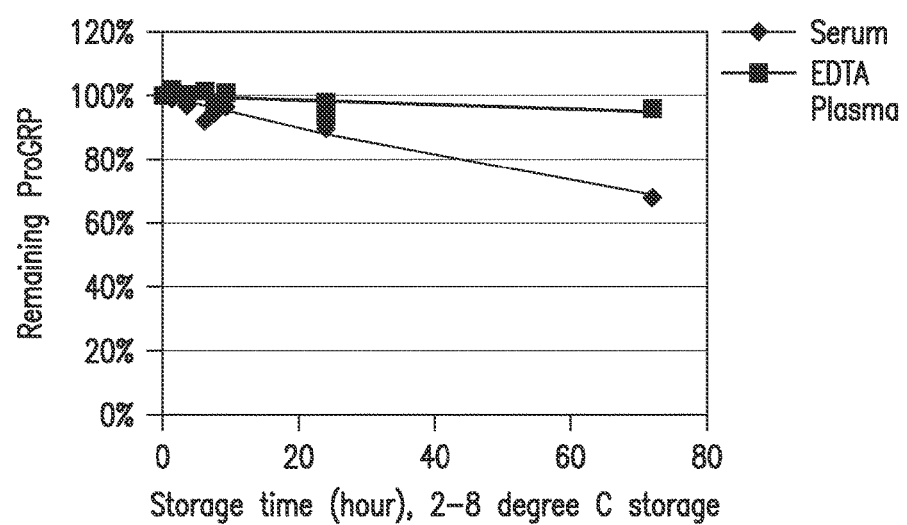
FIG. 9 depicts a plot of the remaining ProGRP (expressed as %) as a function of storage time (expressed in hours) at refrigeration temperature (2 °C.-8 °C.) for ProGRP antigen incubated in samples containing serum (▲) or plasma including EDTA ("EDTA plasma") (■).
Figure 10:
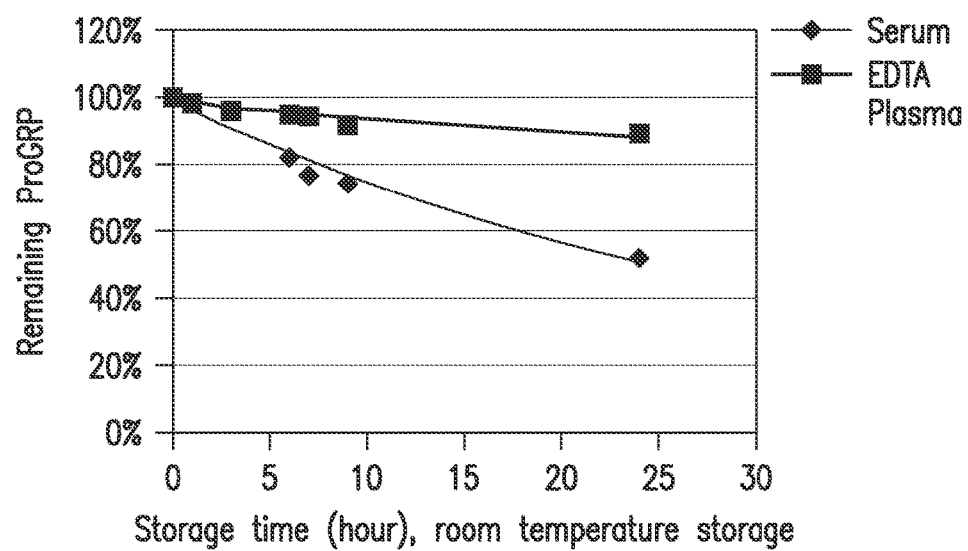
FIG. 10 depicts a plot of the remaining ProGRP (expressed as %) as a function of storage time (expressed in hours) at room temperature for ProGRP antigen incubated in samples containing serum (♦) or plasma including EDTA ("EDTA plasma") (■).

What is claimed:

1. A method of improving stability of Pro-Gastrin-Releasing Peptide 31-98 (ProGRP 31-98 peptide) in a serum sample comprising:
    (a) obtaining a serum sample containing a ProGRP 31-98 peptide from a subject, wherein the serum sample is not dried;
    (b) adding serine protease inhibitor phenylmethylsulfonyl fluoride (PMSF) to the serum sample to form a mixture of PMSF and the serum sample;
    (c) storing the mixture at room temperature, wherein more than 80% of ProGRP 31-98 peptide present in the mixture after step (b) remains in the mixture after 20 hours of storage at room temperature; whereupon the stability of the ProGRP 31-98 peptide is improved as compared to the stability in a serum sample lacking phenylmethylsulfonyl fluoride.

2. The method of claim 1, wherein the phenylmethylsulfonyl fluoride is added to a sample collection vessel after serum is added to the sample collection vessel.

\* \* \* \* \*